United States Patent [19]

Hammitt et al.

[11] 4,058,004
[45] Nov. 15, 1977

[54] APPARATUS FOR MEASURING EROSION PRODUCED BY CAVITATION

[76] Inventors: Frederick G. Hammitt, 1306 Olivia St., Ann Arbor, Mich. 48104; Osman Saleh Mohamed Ahmed, 23 Wildwood Terrace, Glen Ridge, N.J. 07028; Niranjan Rasik Bhatt, 810 Victoria St., Windsor, Conn. 06095; Jia-Bo Gilbert Hwang, 2385-2 Bishop, Ann Arbor, Mich. 48105

[21] Appl. No.: 677,792

[22] Filed: Apr. 16, 1976

[51] Int. Cl.² ............................................ G01N 17/00
[52] U.S. Cl. ........................................................ 73/86
[58] Field of Search ..................... 73/86, 148, 67, 53, 73/194 B, 194 A

[56] References Cited

U.S. PATENT DOCUMENTS

| | | | |
|---|---|---|---|
| 3,218,852 | 11/1965 | Scarpa et al. | 73/194 B |
| 3,240,674 | 3/1966 | Ledwidge | 73/19 |
| 3,538,747 | 11/1970 | Munch | 73/53 |
| 3,834,227 | 9/1974 | Patterson et al. | 73/194 B |
| 3,964,308 | 6/1976 | Scarpa | 73/194 A |

OTHER PUBLICATIONS

Macrosonics Corporation, Cavitation Intensity Measurement in Ultrasonic Tanks, (Aug. 1965) (9 pages).

Primary Examiner—James J. Gill
Assistant Examiner—Anthony V. Ciarlante
Attorney, Agent, or Firm—Olsen and Stephenson

[57] ABSTRACT

Apparatus for sensing pressure pulses developed by the collapse of bubbles in a liquid flow system to enable measurement of the rate of erosion caused to material by cavitation. A sonic transducer, immersed in flowing liquid, generates voltages in response to pressure pulses developed by the collapse of bubbles in the liquid. The voltage representing each bubble collapse is transmitted to electronic equipment. The electronic equipment measures the magnitude of each voltage signal and counts the number of voltage signals representing the number of bubble collapses sensed by the sonic transducer thereby providing data from which the rate of erosion can be calculated.

2 Claims, 4 Drawing Figures

U.S. Patent    Nov. 15, 1977    4,058,004
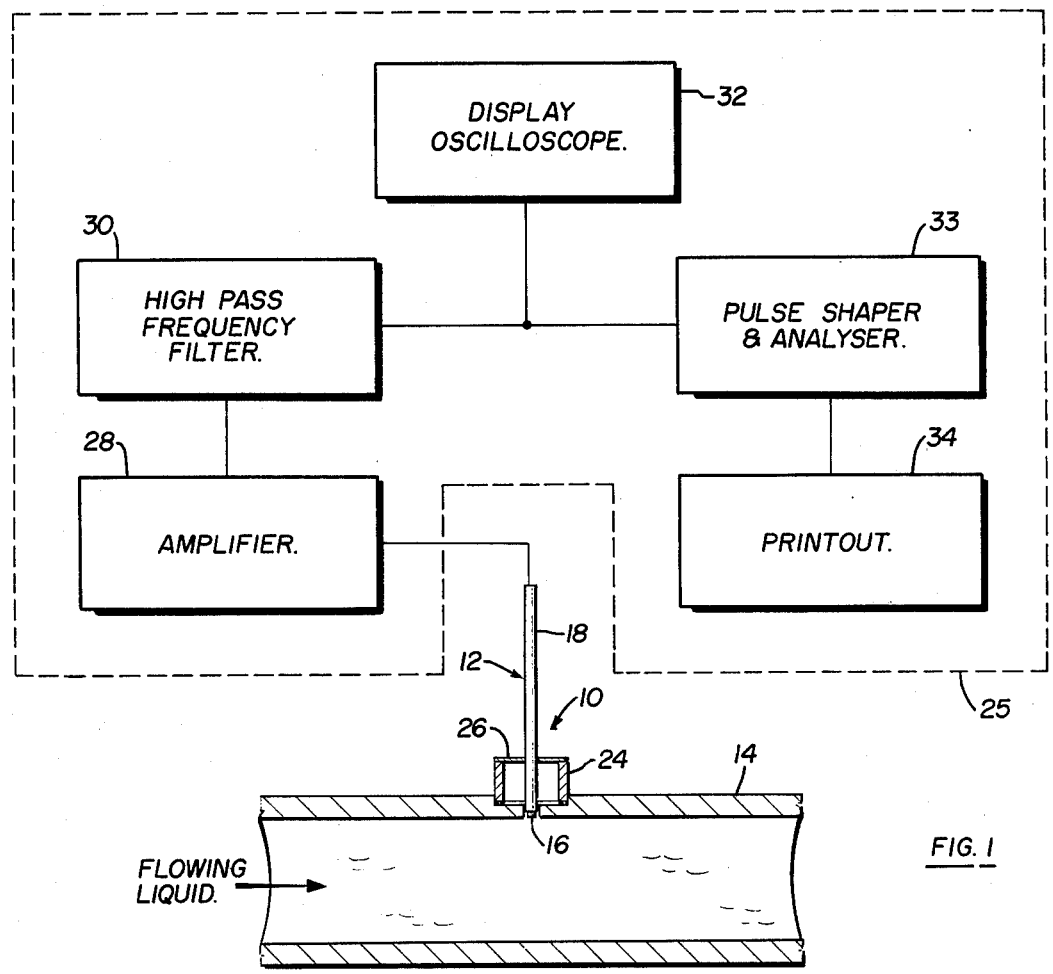
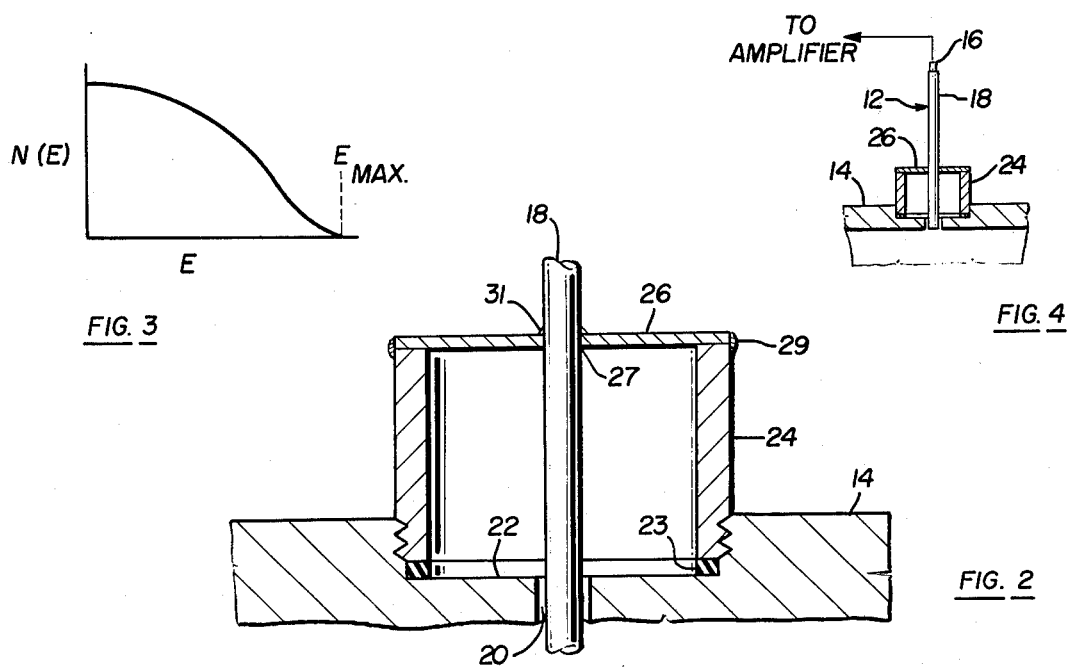

APPARATUS FOR MEASURING EROSION PRODUCED BY CAVITATION

BACKGROUND OF THE INVENTION

The present invention relates to cavitation phenomenon which occurs in flowing liquids and provides apparatus which enables the prediction of the erosion rate of material subjected to the effects of cavitation.

Cavitation is a physical phenomenon occurring in a liquid in which cavities or bubbles are formed when the pressures in certain areas in the liquid approach zero. It is known that cavitation damages the surfaces contacted by the moving liquid. As each bubble collapses, it apparently produces an impulse against the exposed surface causing erosion of the surface.

At the present time, methods for determining erosion rates due to cavitation involve either analytical estimates or large scale long duration field tests. The former are unreliable and the latter are expensive and time consuming.

It is an object of the present invention to provide apparatus for quickly and accurately evaluating the intensity of cavitation in a moving liquid to enable determination of erosion rates due to the effects of cavitation.

SUMMARY OF THE INVENTION

The present invention consists of a sonic transducer immersed in flowing liquid and operable to sense the force exerted when individual bubbles in a cavitation region collapse. The transducer sends a voltage signal, whose strength depends on the magnitude of force sensed by the transducer, to electronic equipment which counts the transmitted signals and which records measurements representative of the pressures exerted by the collapse of bubbles that had been sensed by the sonic transducer. In the preferred form of the invention, the sonic transducer includes a piezoelectric body which is attached to a rod positioned so that the piezoelectric body is mounted flush with the inside of the pipe (through which the liquid is flowing.) The body is thus immersed in the liquid in such a way that a minimum flow disturbance, which would otherwise trigger additional cavitation, is created. The piezoelectric body may, if necessary, be sealed from the liquid by a thin diaphragm so that only a minimum attenuation of the sonic signal is experienced at this point. If the piezoelectric body and liquid are compatible, no such seal may be necessary, in which case the electric leads from the piezoelectric body to the electronic instrumentation are appropriately sealed.

In some cases the temperature of the liquid may be such that it is not appropriate that the piezoelectric body be exposed to this temperature. In such case, the piezoelectric body is secured to the end of the rod remote from the liquid, the end of the rod closest to the liquid being installed flush with the inner pipe wall. The sonic impulses are then transmitted by the rod, acting in the fashion of a "wave-guide", to the piezoelectric body at the far end of the rod, well outside of the liquid and thence in a position where it can be easily maintained at a temperature appropriate to its own operation.

The rod is secured to a flexible diaphragm, which provides the necessary seal, mounted on the body of the pipe through which the liquid is flowing. This arrangement enables high frequency pressure pulses to be readily sensed by the transducer and transmitted to the electronic equipment. The data relating to the number of bubble collapses and their magnitudes can be applied to known relationships so that the rate of erosion of a given material subjected to cavitation can then be determined.

Thus, the present invention enables the ready evaluation of the ability of a particular material or structure to resist erosion due to cavitation.

Further objects, features and advantages of the present invention will become apparent from a consideration of the following description when taken in connection with the appended claims and the accompanying drawing in which:

FIG. 1 is a schematic view of the apparatus of the present invention;

FIG. 2 is an enlarged fragmentary sectional view of a portion of the apparatus shown in FIG. 1;

FIG. 3 is a graph representing the data collected by the apparatus of this invention; and FIG. 4 is a schematic view, like FIG. 1, showing another form of the apparatus of this invention.

Referring to the drawing, the sensing apparatus of the present invention, shown generally at 10, consists of a sonic transducer 12 extending into a pipe 14 and operable to sense the collapse of bubbles in fluid flowing through the pipe 14. The sonic transducer 12, in the illustrated embodiment of the present invention, consists of a body 16 of piezoelectric material attached to the end of a rod 18. The piezoelectric body 16 is preferably of ceramic type.

The transducer 12 is mounted to extend diametrically into the pipe 14, as shown in FIG. 2. An opening 20, formed in the pipe 14, provides a passageway through which the rod 18 extends. A plug hole 22 is formed in the pipe 14 in alignment with the opening 20 and is threaded so that a plug 24 can be threadably mounted therein and sealed such as by a gasket 23. A flexible diaphragm member 26 formed of thin metal or other flexible material is illustrated for mounting the rod 18 on the plug 24 for a purpose to appear presently. The member 26 has a central opening 27 and is secured at its periphery, such as by welding 29, to the plug 24. The rod 18 projects through the opening 27 and is there secured to the diaphragm 26 such as by welding 31. This arrangement provides for sealed attachment of the sonic transducer 12 to the pipe 14. It also enables the transducer 12 to efficiently sense and transmit high frequency pulses. The flexible nature of the member 26 is not so essential in the FIG. 1 embodiment of the invention as it is in a modified form of the invention described hereinafter.

The sonic transducer 12 is connected to an electronic system 25, comprised of conventional electronic components, which functions to display on a chart the number and magnitude of pulses generated by the body 16 over a given period of time. The system 25 includes an amplifier 28 which amplifies the voltage signals developed by the piezoelectric body 16. The amplified pulse is then transmitted through a high-pass frequency filter 30 which removes low frequency signals that may be due to outside effects. The high-pass filter 30 also removes the pulses which represent low intensity pressure collapses that have no damaging effect on the metal being tested. The output of the high-pass frequency filter 30 is then projected on a display oscilloscope 32 so that the resulting image can thus be observed and photographed. The output of the high-pass frequency filter 30 is also transmitted to a pulse shaper and analyzer 33 which shapes the pulse to the form required for the proper functioning of the analyzer. The analyzer sorts the output of the high-pass frequency filter into pulses of varying magnitude. The sorted pulses are then transmitted to the printout 34 which produces a chart displaying the number and magnitude of pulses generated over a given period of time.

The erosion rate (E.R.) of a given material can be calculated using a relationship such as E.R. = $C_1(E_t - C_2)^n$ where $C_1$, $C_2$ and n are constants whose values are determined from empirical tests. $E_t$ is the total pulse energy delivered to the sonic transducer 12 over a given period of time and is determined by calculating the area beneath the plotted curve N(E) vs. E, as shown in FIG. 3. N(E) is a value representing the number of pulses counted at a given energy level and E is a value representing the energy level at which the pulses are counted.

In FIG. 4, a modified form of the apparatus 10 is shown in which the body 16 is on the end of the rod 18 remote from the pipe 14. The near end of the rod 18 projects into the opening 20 so as to be substantially flush with the inner surface of the pipe 14. The apparatus shown in FIG. 4 is identical to the apparatus 10 except for the location of the body 16 and is useful in cases in which the temperature of the liquid in pipe 14 is either extremely high or extremely low.

It can thus be seen that apparatus for measuring the force and number of bubble collapses in a cavitation region is provided which enables accurate and quick prediction of the rate of erosion caused to material subjected to cavitation. The sonic transducer 12, which includes the piezoelectric body 16 and the rod 18, senses the collapse of individual bubbles and transmits pulses to electronic equipment 25 which records representative measurements of the force exerted by the bubble collapse and the number of bubble collapses sensed by the piezoelectric material 16. The electronic equipment 25 produces a chart displaying the number and magnitude of pulses sensed by the transducer 12. Using known relationships and this data, the rate of erosion of material subjected to cavitation can be determined.

What is claimed:

1. Apparatus for sensing the collapse of cavitation bubbles in liquid flowing through a conduit having an inner surface and an opening extending through said surface to provide communication with said liquid, said apparatus comprising an elongated pulse transmitting rod member extending into said opening in a position in which the inner end thereof is substantially flush with said inner conduit surface adjacent said opening, the outer end of said rod member being disposed outside said conduit a predetermined remote distance from said conduit in a location in which said outer end can be maintained at a temperature substantially unaffected by the temperature of said liquid and said conduit, a diaphragm type member having a central opening and being mounted on said conduit, said rod member extending through said opening and being affixed to said diaphragm member in a sealing relationship therewith, said diaphragm member enabling transmission of relatively undistorted and unattenuated pulses through said rod member, and a transducer mounted on said outer end of said rod member and operable to develop electrical signals in response to a sensing of pulses transmitted through said rod and caused by forces in said conduit resulting from the collapse of cavitation bubbles in said liquid.

2. Apparatus according to claim 1 wherein said transducer comprises a body of piezoelectric material mounted on said rod and operable to generate electrical signals representing cavitation in said liquid.

* * * * *